(12) United States Patent
Hodzic et al.

(10) Patent No.: US 9,008,273 B2
(45) Date of Patent: Apr. 14, 2015

(54) SYSTEM FOR ANALYZING A GRANULATE FOR PRODUCING A PHARMACEUTICAL PRODUCT

(75) Inventors: Aden Hodzic, Graz (AT); Peter Laggner, Graz (AT); Walter Tritthart, Stainz (AT)

(73) Assignee: Bruker AXS GmbH, Karlsruhe (DE)

( * ) Notice: Subject to any disclaimer, the term of this patent is extended or adjusted under 35 U.S.C. 154(b) by 436 days.

(21) Appl. No.: 13/577,439

(22) PCT Filed: Feb. 8, 2011

(86) PCT No.: PCT/EP2011/000586
§ 371 (c)(1),
(2), (4) Date: Nov. 26, 2012

(87) PCT Pub. No.: WO2011/095364
PCT Pub. Date: Aug. 11, 2011

(65) Prior Publication Data
US 2013/0077755 A1  Mar. 28, 2013

(30) Foreign Application Priority Data
Feb. 8, 2010 (EP) .................................. 10152977

(51) Int. Cl.
*G01N 23/00* (2006.01)
*G01N 23/201* (2006.01)
*G01N 23/20* (2006.01)

(52) U.S. Cl.
CPC .............. *G01N 23/201* (2013.01); *G01N 23/20* (2013.01)

(58) Field of Classification Search
USPC .......................................................... 378/88
See application file for complete search history.

(56) References Cited

U.S. PATENT DOCUMENTS

2008/0165354 A1* 7/2008 Rantanen et al. ............. 356/301

OTHER PUBLICATIONS

Martino et al, "Phase Behavior and Microstructure of Nonaqueous Microemulsions". J. Phys. Chem. 1990, 94, 1627-1631.*
Han Young Chung et al., "Factors affecting the apparent solubility of ursodeoxycholic acid in the grinding process", International Journal of Pharmaceutics 255 (2003) 49-56.
Michelle R. Jenquin et al., "Characterization of acrylic resin matrix films and mechanisms of drug-polymer interactions", International Journal of Pharmaceutics, 101 (1994) 23-34.
Peter Laggner et al., "Characterization by Small-and Wide-Angle X-Ray Scattering", Solid State Characterization of Pharmaceuticals. Eds. A. and M. Zakrzewski. Assa International, Danbury 2005.
Li Zhihong et al., "Determination of specific surface of silica xerogels by SAXS", Chinese Science Bulletin vol. 45 No. 15 Aug. 2000.

* cited by examiner

*Primary Examiner* — Phillip A Johnston
(74) *Attorney, Agent, or Firm* — Paul Vincent

(57) ABSTRACT

An apparatus for analyzing a granulate for producing a pharmaceutical product has a data receiving unit adapted for receiving X-ray diffraction data indicative of a scattering of X-rays irradiated onto the granulate, a processor unit adapted for processing the X-ray diffraction data to derive information indicative of a compressibility and/or a dissolution characteristic of the granulate, and a control unit adapted for controlling a process of producing a pharmaceutical product based on the derived information.

19 Claims, 8 Drawing Sheets

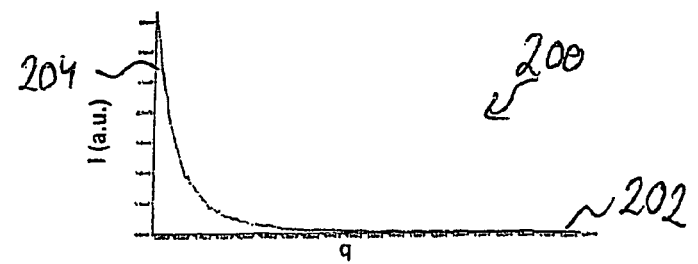
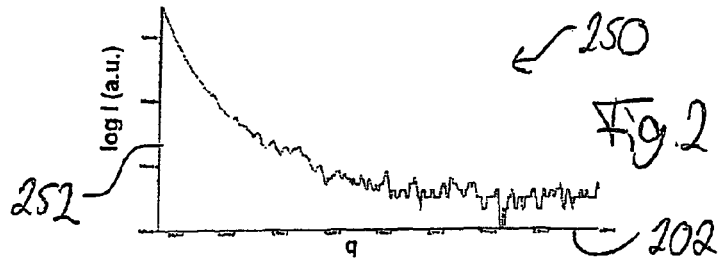
Fig. 2
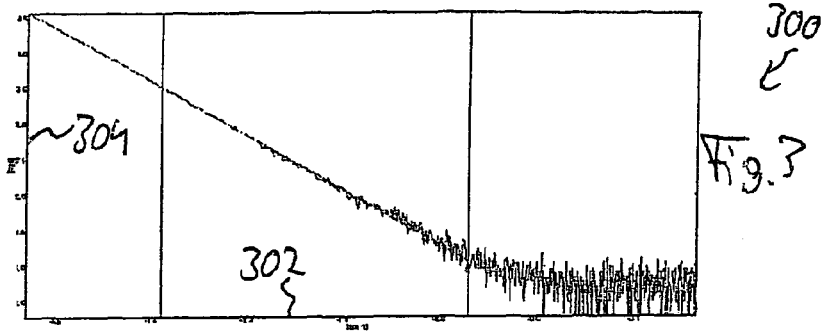
Fig. 3
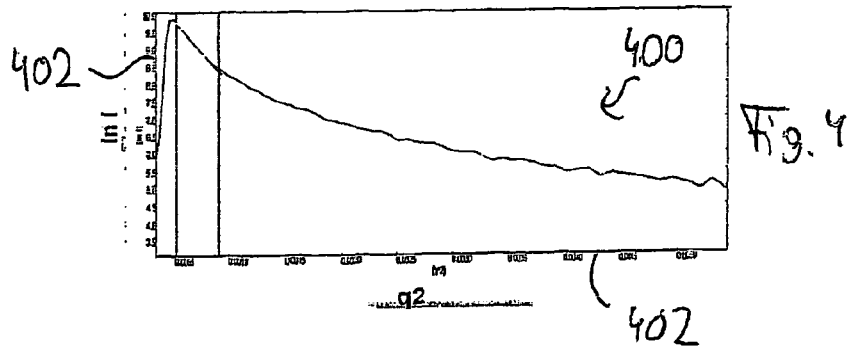
Fig. 4
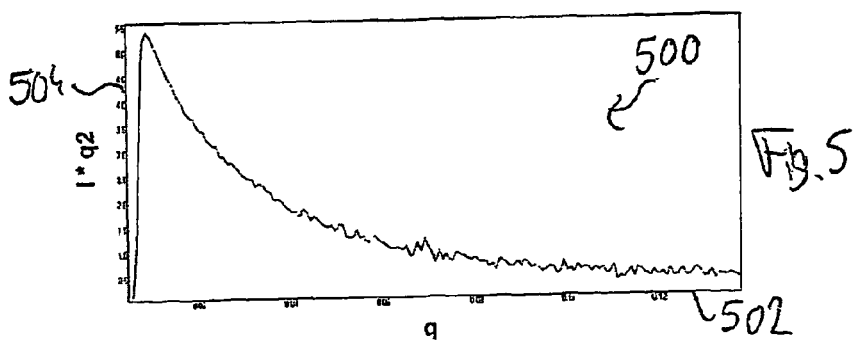
Fig. 5

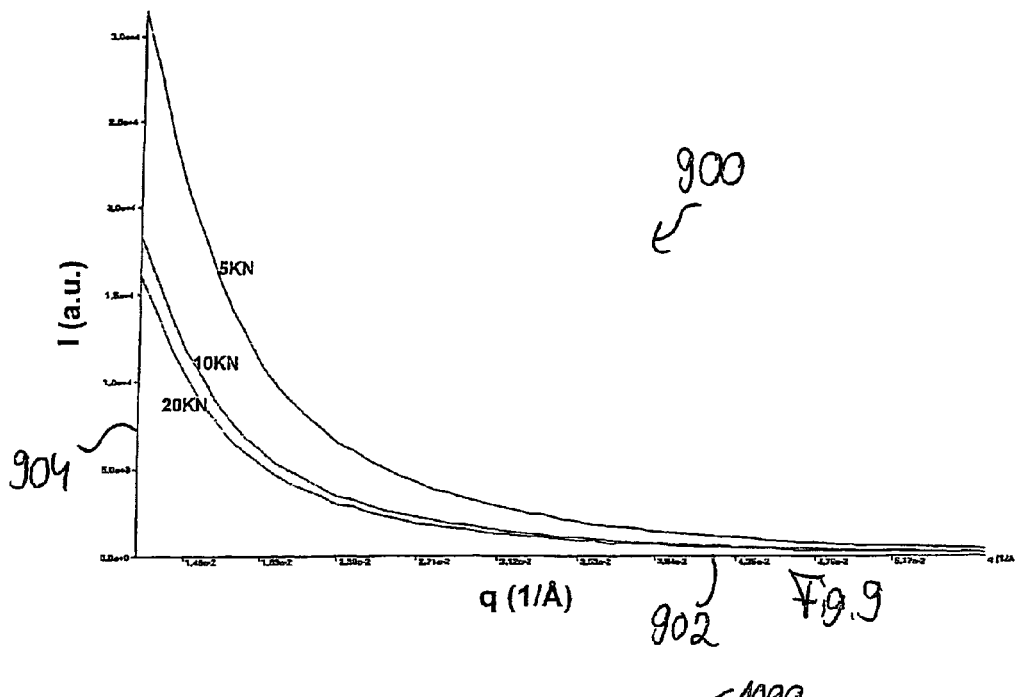
Fig. 9
| Samples | K2 | Q | K/Q (Å²/Å³) | L=4Q/πK (Å) |
|---|---|---|---|---|
| 5KN | 0.0013 | 0.0363± 0.0005 | 0.0245±0.0005 | 35.6 ± 0.05 |
| 10KN | 0.0010 | 0.0330± 0.0005 | 0.0190±0.0005 | 42.5 ± 0.05 |
| 20Kn | 0.0008 | 0.0322± 0.0005 | 0.0176±0.0005 | 51.3 ± 0.05 |
Fig. 10
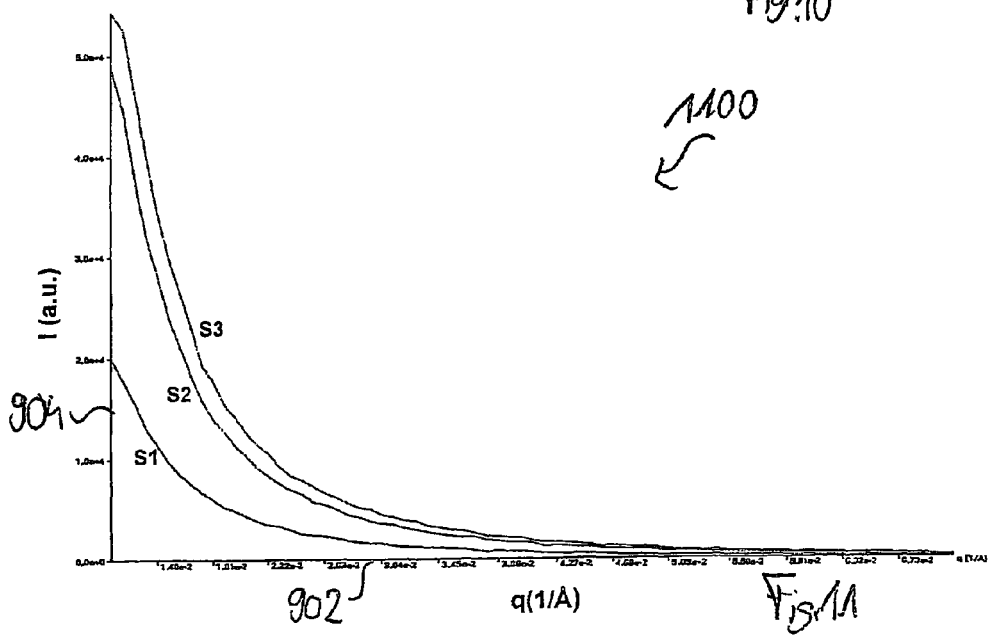
Fig. 11

| Powder Samples SpinCap | K2 | Q | K/Q (Å²/Å³) | L=4Q/πK (Å) |
|---|---|---|---|---|
| S1 | 0.0003 | 0.0417 ± 0.001 | 0.0065 ± 0.0005 | 177,10 ± 0.1 |
| S2 | 0.0007 | 0.0936 ± 0.001 | 0.0079 ± 0.0005 | 170,30 ± 0.1 |
| S3 | 0.0012 | 0.1184 ± 0.001 | 0.0099 ± 0.0005 | 125,70 ± 0.1 |

| CBZ SpinCap | K2 | Q | K/Q (Å²/Å³) | L=4Q/πK (Å) |
|---|---|---|---|---|
| S1 (bad) | 0.0010 | 0.0730±0.006 | 0.0130 ± 0.006 | 93 ± 0.9 |
| S2 (good) | 0.0052 | 0.2400±0.006 | 0.0220± 0.006 | 58.8 ± 0.9 |

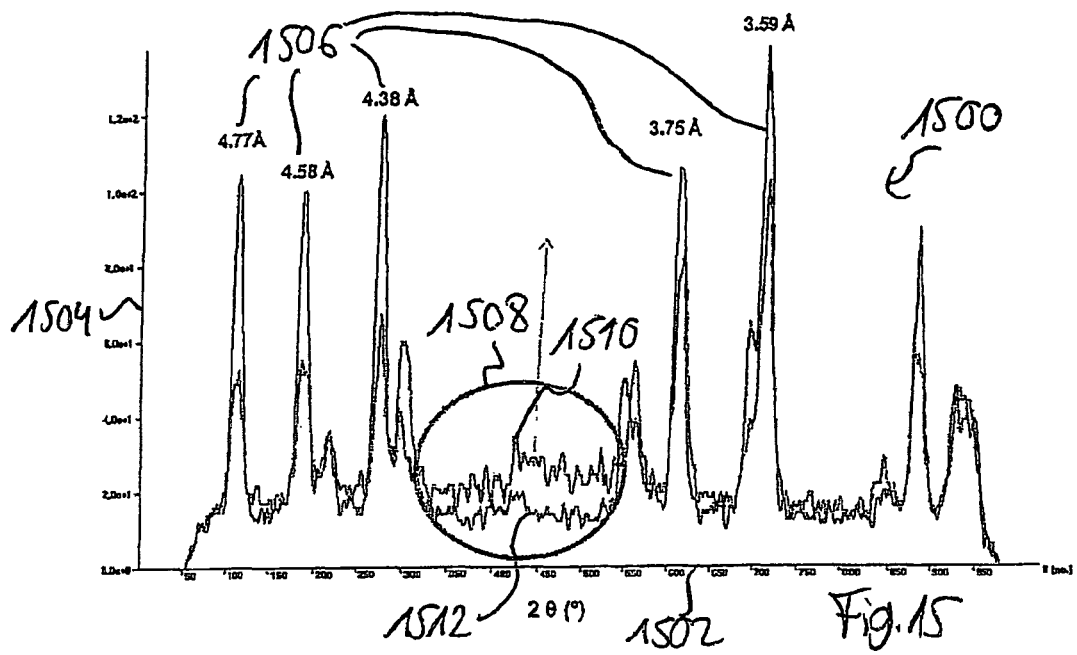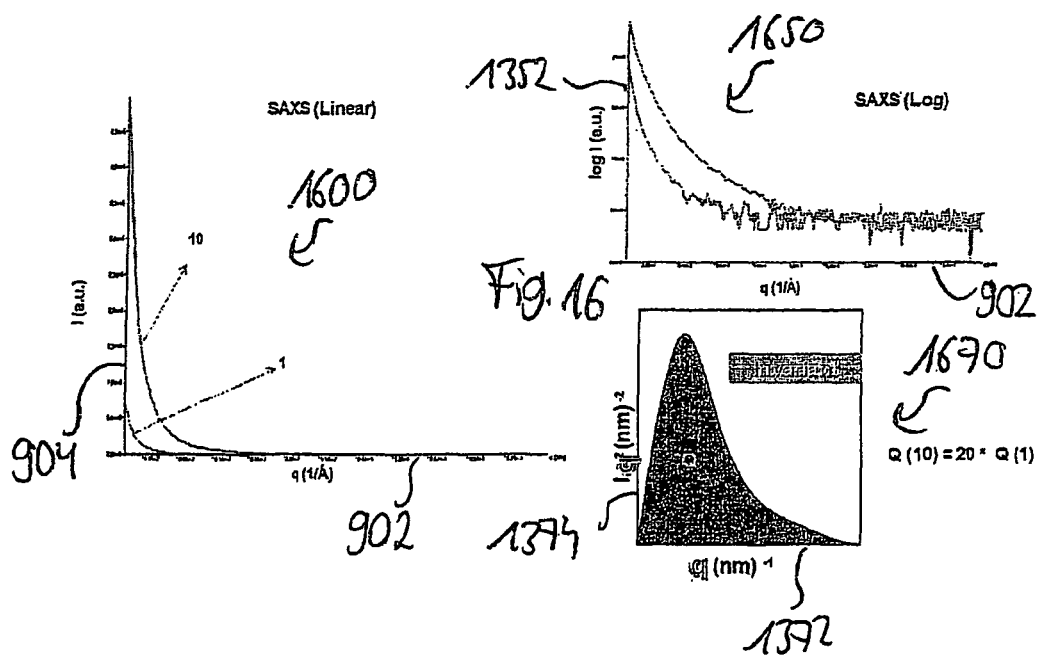

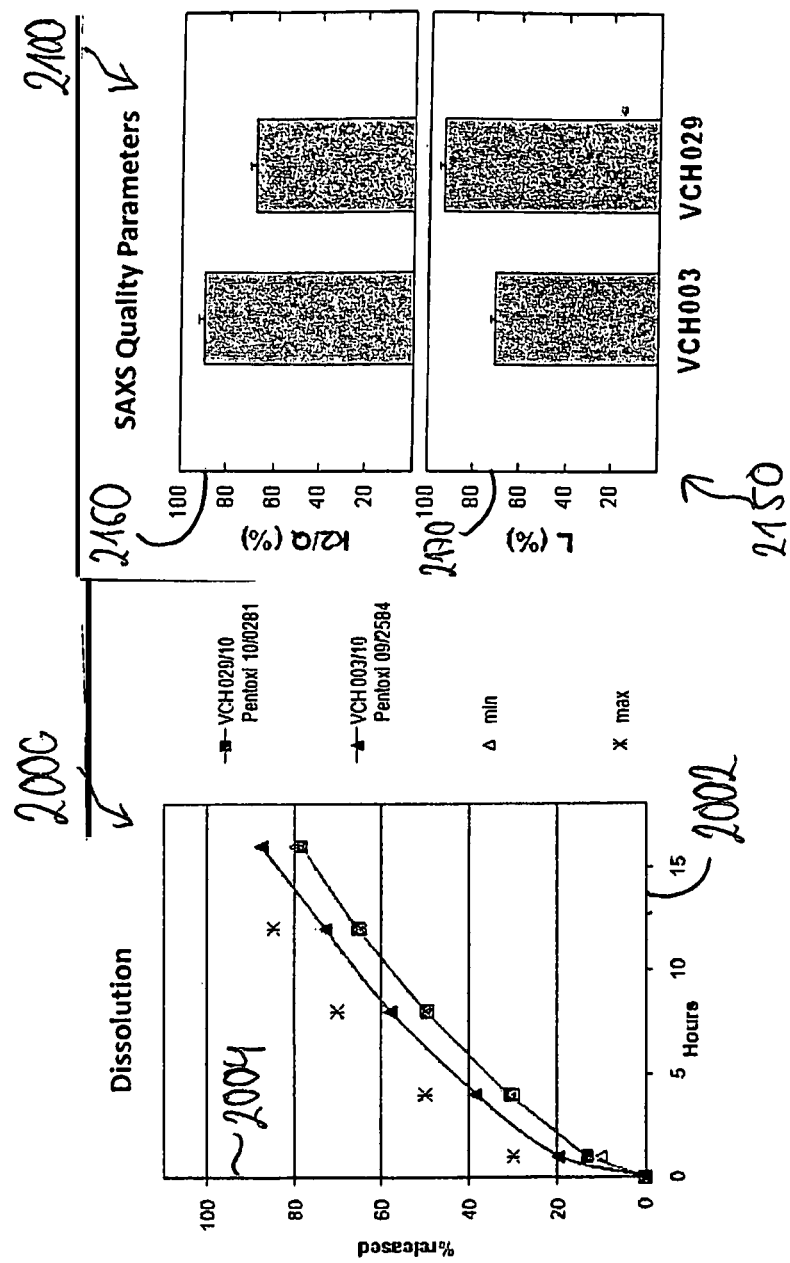

SYSTEM FOR ANALYZING A GRANULATE FOR PRODUCING A PHARMACEUTICAL PRODUCT

This application is the national stage of PCT/EP2011/000586 filed on Feb. 8, 2011 and also claims Paris Convention priority of EP 10 152 977.4 filed on Feb. 8, 2010.

BACKGROUND OF THE INVENTION

The invention relates to an apparatus for analyzing a granulate for producing a pharmaceutical product.

Moreover, the invention relates to a method of analyzing a granulate for producing a pharmaceutical product.

Beyond this, the invention relates to a program element.

Furthermore, the invention relates to a computer-readable medium.

It is conventionally known to apply SAXS (small-angle X-ray scattering) and WAXS (wide-angle X-ray scattering) for analyzing samples.

P. Laggner, M. Kriechbaum, M. Rappolt, G. Pabst, H. Amenitsch, A. Johs, K. Lohner, D. Zweytick, R. Koschuch, and P. Abuja, 2005, "Pharmaceutical solid-state characterization by small- and wide-angle x-ray scattering", In: "Solid State Characterization of Pharmaceuticals", Eds. A. and M. Zakrzewski, Assa International, Danbury, chapter 12, discloses theoretical considerations with regard to the analysis of porous systems measured by SAXS.

Zhihong, S. Jihong, W. Dong, S. Yuhan, L. Yi, S. Wenjun, and D. Baozong, 2000, "Determination of specific surface of silica xerogels by SAXS", Chinese Science Bulletin, 45 (15): 1386-1390, discloses to apply SAXS to silica xerogels.

The action of drugs is based on the presence of an active principle which may also be denoted as a therapeutically useful substance or a physiologically active substance. The active principle may be mixed with other substances, which may be therapeutically active itself or are needed as adjuvants for the manufacture of a proper dosage form. With pharmaceutical operations in which powders are involved, it is important that the powder has good flow properties. Many therapeutically useful compounds, however, cannot easily be processed to dosage forms, particularly tablets or capsules, because they have an inherent, unsatisfactory flow behavior. Therefore, according to well established pharmaceutical practice, before tableting, those substances are first converted into a granulate which possesses the desired flow properties. In wet granulation, the active principle is mixed with a granulation liquid, which often is water and where special granulation adjuvants may be added. According to well known procedures, a wet mass is passed through a sieve grid, dried, milled and sieved. The thus resulting granulate may be used for instance as ingredient in a tableting mixture, but when capsules are chosen as the dosage form, the granulate can be used as such.

A granulate compressibility and compactibility (appropriate or inappropriate) is conventionally tested mechanically. The observation of similar granulates physical properties are sieve analysis and laser diffraction. The methods determine rather a grain size distribution, which is not a direct indication for granulate homogeneity, total inner surface and nanoporosity. Hence, all of these methods are dissatisfying in terms of the granulate compressibility control.

Furthermore, $N_2$ absorption (BET) provides also surface analytics of powders. The advantage of the method is determination of the absolute surface values. The disadvantage of BET is a long time required for measurements, whereby not a "total" inner surface can be determined.

Conventionally, it is difficult to properly investigate the properties of pharmaceutical granulates for use as a base material for the production of pharmaceutical products.

It is an objective of the invention to provide an efficient way of analyzing a granulate based on which a pharmaceutical product is manufacturable.

SUMMARY OF THE INVENTION

In order to achieve the objective defined above, an apparatus for analyzing a granulate for producing a pharmaceutical product, a method of analyzing a granulate for producing a pharmaceutical product, a program element, and a computer-readable medium according to the independent claims are provided.

According to an exemplary embodiment of the invention, an apparatus for analyzing a granulate for producing a pharmaceutical product is provided, the apparatus comprising a data receiving unit adapted for receiving X-ray diffraction data (particularly, both Small Angle X-Ray Scattering data (SAXS) and Wide Angle X-Ray Scattering data (WAXS) are received) indicative of a scattering of X-rays irradiated onto the granulate, a processor unit adapted for processing the X-ray diffraction data to derive information indicative of a compressibility and/or a dissolution characteristic of the granulate (particularly, both compressibility and dissolution characteristic of the granulate are derived), and a control unit adapted for controlling a process of producing a pharmaceutical product (for instance a process of pressing tablets using the granulate material) based on the derived information.

According to another exemplary embodiment of the invention, a method of analyzing a granulate for producing a pharmaceutical product is provided, wherein the method comprises receiving X-ray diffraction data indicative of a scattering of X-rays irradiated onto the granulate, processing the X-ray diffraction data to derive information indicative of a compressibility and/or a dissolution characteristic of the granulate (simultaneously determination of polymorphic states by WAXS) and controlling a process of producing a pharmaceutical product based on the derived information.

According to still another exemplary embodiment of the invention, a program element (for instance a software routine, in source code or in executable code) is provided, which, when being executed by a processor (such as a microprocessor or a CPU), is adapted to control or carry out a method having the above mentioned features.

According to yet another exemplary embodiment of the invention, a computer-readable medium (for instance a CD, a DVD, a USB stick, a floppy disk or a harddisk) is provided, in which a computer program is stored which, when being executed by a processor (such as a microprocessor or a CPU), is adapted to control or carry out a method having the above mentioned features.

Data processing which may be performed according to embodiments of the invention can be realized by a computer program, that is by software, or by using one or more special electronic optimization circuits, that is in hardware, or in hybrid form, that is by means of software components and hardware components.

The term "granulate" or "granulate material" may particularly denote a conglomeration of discrete solid, macroscopic particles. The constituents that compose granular material can be large enough such that they are not subject to thermal motion fluctuations. Granulates can have a dimension between 5 nm and 1000 μm. More particularly, a dimension of granulates may be in the order of magnitude of micrometers, for instance between 1 μm and 100 μm, more particularly between 5 µm and 20 µm. Thus, the dimension of granulates may be large as compared to the resolution of X-ray, which is in the order of magnitude of nanometers. A sample of granulate material may then scatter simultaneously in the small and wide angular range.

The term "pharmaceutical product" may particularly denote a medication in an administerable form such as a tablet, a capsule, or any other appropriate dosage form.

The term "compressibility" or compactibility may particularly denote a measure of the relative volume change of a solid or powder as a response to an applied pressure (or mean stress) change, i.e. the degree to which something is compressible or compactable.

The term "dissolution characteristic" may particularly denote a measure quantifying the ability of a substance to form a homogeneous mixture with a solvent. This can be explained as a breakdown of the solid constitution (for instance a crystal lattice structure) into individual ions, atoms or molecules and their transport into the solvent. An example for a parameter being indicative of the dissolution characteristic of a solute is the rate of dissolution, i.e. an amount (for instance a mass) of dissolved material per time. The dissolution characteristic may indicate to which degree a medication such as a tablet can be dissolved within a physiological object such as a human being. For example, such a dissolution may take place in the gastric, in the intestine, etc.

According to an exemplary embodiment of the invention, a system is provided which uses X-ray diffraction for analyzing granulates used for producing pharmaceutical products such as tablets. It has been surprisingly recognized that X-ray scattering data allow to accurately predict compressibility and dissolution, respectively, of the granulate and simultaneously. With regard to the dissolution properties, this may concern particularly the dissolution in gastric juice. It has for instance been recognized that, the better the compressibility, the better is the solubility in gastric juice. Thus, the suitability of a granulate charge for the manufacture of a medication in dosage form (for instance tablets) may be determined by a very fast measurement with high precision. Particularly the combination of different items of information derivable from X-ray scattering may allow to discover at the same time physical properties of the granulate (particularly by Small Angle X-Ray Scattering, SAXS) such as compressibility/dissolution characteristics and to simultaneously monitor physiological activity of the substance (for instance by Wide Angle X-ray Scattering, WAXS). Therefore, the analysis architecture according to an embodiment of the present invention is a powerful tool for process control in pharmaceutical engineering.

In the following, further exemplary embodiments of the apparatus will be explained. However, these embodiments also apply to the method, to the computer-readable medium and to the program element.

Exemplary embodiments of the invention may be used for quality control in pharmaceutical engineering. This particularly allows a quality control of a pharmaceutical agent coated with a gastric juice resistant polymer. During a manufacturing process, a tablet may be pressed from such a granulate if the compressibility properties fit. It may also be determined whether the material of the tablet actually meets requirements of solubility in the stomach and the intestine. The tablets should be resistant to a dissolution in the gastric and should not be dangerous for the gastric mucosa lining.

Data receiving unit, processor unit, and control unit may each be individual units having processing capability (such as a central processing unit, microprocessor, etc.). It is however also possible that two or more of these (and other) units are combined to a single processing entity (such as a central processing unit, microprocessor, etc.).

Inspection of a pharmaceutical manufacturing process by X-ray diffraction of a granulate or a product thereof may be performed once (for instance directly before pressing tablets from the pharmaceutical granulate) or multiple times (allowing to monitor a larger part of or even the entire manufacturing process).

According to an exemplary embodiment, the processor unit may be adapted for processing the X-ray diffraction data to derive information regarding different solid components of a granulate, i.e. different material constituents. For example, a granulate consisting of multiple solid components may comprise one or more physiologically active substances as well as optionally associated material, a tablet matrix, or the like. It has been surprisingly recognized that the analysis of a granulate for pharmaceutical monitoring works properly even in the presence of granulates being formed of multiple different solid components, not only being formed of one homogeneous material. For instance, pharmaceutical granulates having a core (for instance of a physiologically active substance) and a shell (for instance a protection against dissolution by gastric juice) can be characterized with regard to both core and shell at the same time. Since X-ray diffraction is sensitive to the electron density distribution, physical properties such as compressibility and dissolution characteristics are derivable regardless of the number of different species in a granulate sample. Therefore, without the need of a complex splitting of different species individually in an X-ray scattering spectrum, an overall information of the properties of the granulate material can be obtained.

In an embodiment, the data receiving unit is adapted for receiving X-ray diffraction data resulting from Wide Angle X-Ray Scattering (WAXS). In this context, the term Wide Angle X-Ray Scattering may particularly denote an angular range of, for instance, 16° to 27° relative to an incident axis of X-rays. A WAXS spectrum is kind of a fingerprint of the crystalline forms (active pharmaceutical ingredient or excipients) of the pharmaceutical granulate which can be inspected by analyzing individual peaks of the spectrum. Conversion from a crystalline phase to an amorphous phase, or vice versa, during the pharmaceutical manufacture procedure may be seen in the spectrum as a shift of intensity from discrete peaks to the spectral background, or vice versa. Therefore, the monitoring of the spectral fingerprint of the active pharmaceutical ingredient may allow the confirmation that the active pharmaceutical ingredient has or has not been deteriorated or inactivated by a treatment of pharmaceutical engineering, for instance during the manufacture of a tablet. Particularly, the WAXS spectrum allows determining whether the active pharmaceutical ingredient has remained in a crystalline phase or has been converted into another polymorphic state or an amorphous phase. This information with regard to the crystallinity of the solid has also an impact on the characteristics according to which the active pharmaceutical ingredient operates physiologically.

The processing unit may be more particularly adapted for processing Wide Angle X-Ray Scattering data to derive information indicative of a quality-related property of a physiologically active substance of the granulate. Thus, a property indicative of a quality of the substance concerning the production of a pharmaceutical product may be derived. More particularly, a morphology of the substance may be characterized based on the measured data. In this context, morphology may relate to the shape, size, texture and phase distribution of the substance or components thereof. It may include the information whether the substance is in a crystalline or in an amorphous state.

According to another exemplary embodiment, the data receiving unit may be adapted for receiving X-ray diffraction data resulting from Small Angle X-Ray Scattering (SAXS). SAXS can be considered as a complementary method with regard to WAXS. It allows a physical determination of properties such as the compressibility of the tablet. For example, experiments may be carried out correlating the compressibility (as determined by, for instance, pressing experiments) with the behavior of the X-ray spectrum. Such data can be stored, for instance in the form of a database or a lookup table, to be accessible by a process monitoring system to rapidly determine compressibility from a spectrum of a sample under test. Small angle measurement data are indicative of inhomogeneities of the sample. An angular range of Small Angle X-Ray Scattering can be for instance between 0° and 8°, particularly between 0.06° and 8°, with regard to a direction defined by an incident beam.

More particularly, still referring to the SAXS measurement, the processor unit may be adapted for processing the X-ray diffraction data to derive one or more parameters meaningful for pharmaceutical engineering, for instance by fitting an X-ray scattering curve using theoretical considerations given below in more detail.

For example, the second momentum integral of a measurement spectrum, a Porod constant, deviation from an ideal behavior in accordance with Porod's law, an average correlation length, etc. can be determined. The second momentum integral of the measurement spectrum may be considered as a quality parameter indicating how suitable the granulate is compressible for forming tablets. The Porod constant, particularly when taken in combination with the second momentum integral, can also be considered as a meaningful source of information, for instance can indicate the dissolution characteristics. With regard to the Porod theory, not only the value of the Porod constant, but also deviations from an expected Porod behavior may characterize the granulate in the context of pharmaceutical engineering. For example, a positive or negative Porod deviation may provide such information. The Porod constant can be derived from a slope of the measurement signal and can be estimated according to Porod's theory. However, since the Porod's theory holds general for two phases (i.e. air and one solid phase), deviations from the Porod law due to the presence of multiple solid components on the nano-scale allows obtaining valuable additional information with regard to this multi-solid phase system. Particularly, the invariant (Q) may be considered as a quality control parameter. K/Q may be considered as a parameter which is directly proportional to the total inner surface, where K is the Porod constant. Average correlation length L can be used as a parameter which is direct proportional to the nanoporosity.

As a general decision criteria, whether a ratio between the invariant value of a granulate charge under analysis and the invariant value of a reference granulate exceeds a first threshold value (for instance is larger than 10), the granulate charge under analysis can be accepted. Additionally or alternatively, if a ratio between the invariant value of a granulate charge under analysis and the invariant value of a reference granulate is below a second threshold value (for instance is smaller than 5), the granulate charge under analysis can be rejected. Additionally or alternatively, if a ratio between the invariant value of a granulate charge under analysis and the invariant value of a reference granulate is between the first and the second threshold value, a measure for quality improvement may be applied (for instance a refinishing operation may be applied) or the decision regarding acceptance/rejection may by delegated to a user operating the apparatus.

Even more particularly, the processor unit may be adapted for processing the X-ray diffraction data to derive information indicative of a quality of the granulate based on an intensity in an X-ray diffraction spectrum. As a rule of thumb, the higher the intensity in a SAXS spectrum, the better are the properties with regard to compressibility of the granulate for forming tablets.

In a preferred embodiment, SAXS and WAXS are synergetically combined in the context of pharmaceutical engineering, and this may also be denoted as SWAXS (Small and Wide Angle X-ray Scattering). The combination of these two analytical tools for characterizing manufacturability of tablets from a granulate has the advantage that complementary information with regard to physical (SAXS) and physiological (WAXS) properties of a pharmaceutical granulate can be obtained in a very short time. Thus, a very simple apparatus can be integrated in a process line for monitoring a pharmaceutical process.

The apparatus may comprise an X-ray source adapted for irradiating the granulate with the X-Rays. The X-Rays may have typically 8 keV but any other suitable X-ray energy can be used (such as synchrotron radiation, for instance at an energy of 16 keV). This corresponds to a penetration depth in a sample which is sufficient for most applications. At the same time, this small energy allows for a gentle investigation of the pharmaceutical composition.

The apparatus may comprise a granulate container for accommodating the granulate. The granulate container may be rotatable during acquiring the X-ray diffraction data. It has been surprisingly recognized that a rotation of a sample during the X-ray investigation improves the significance of the result. Without wishing to be bound to a specific theory, it is presently believed that this rotation averages out orientational artifacts and at the same time maintains the useful information with regard to compressibility and dissolution characteristic of the sample. Therefore, rotating the sample holder during acquisition of the measurement data may increase the accuracy of the results. The rotation axis may be perpendicular to an incident direction of the X-rays. By rotating the capillary filled with granulate during the X-ray measurements, the resolution of the analysis may be improved, statistical effects may be averaged out, and the measurement time may be reduced.

In an embodiment, the apparatus may comprise a granulate container for accommodating the granulate and may be adapted for subjecting the granulate to a predefined pressure profile during acquiring the X-ray diffraction data. Such a pressure profile may be a predefined reference pressure value or may be a sequence of different pressure values to be applied to the sample in a predefined order. It has been recognized that the application of pressure during the X-ray acquisition increases the basis of data for deriving characteristics with regard to compressibility and dissolution of a sample. Therefore, it is highly appropriate to acquire measurement data according to X-ray scattering while simultaneously varying the pressure. The use of a pressure cell, particularly a high pressure cell, allows to derive information with regard to the behavior of the material under pressure.

Additionally or alternatively, the granulate container may be adapted for subjecting the granulate to a predefined temperature profile during acquiring the X-ray diffraction data. Such a temperature profile may be a predefined reference temperature value or may be a sequence of different temperature values to be applied to the sample in a predefined order. Also a variation of the temperature may allow to obtain complementary information with regard to the sample. The variation of the temperature allows to perform calorimetric measurements and particularly the investigation of possible phase transitions of the material depending on the temperature.

Also the combination of pressure scans and temperature scans, i.e. applying a two-dimensional profile of external parameters, is highly advantageous for further improving the basis of information for evaluating the data in terms of pharmaceutical engineering.

In an embodiment, the apparatus may be adapted to be operable in-line of the process of producing the pharmaceutical product. An in-line implementation can be realized by integrating a measurement instrument directly in the line of the manufacture of a pharmaceutical product such as a tablet. The manufactured pharmaceutical granulate based on which a tablet should be pressed within the line can be guided during these production steps through an X-ray scattering device so that the actually processed material can be measured during the manufacturing process. Therefore, a direct feedback with regard to physical and/or physiological parameters and properties of the granulate can be obtained. In case of deviations of actual material parameters in terms of compressibility, dissolution properties, properties of the pharmaceutical active substance, etc. from desired values, a pharmaceutical process may be correspondingly adapted in the light of these measurement results. For example, if the quality turns out to be unacceptable, the process can be stopped so as to avoid high rejections of produced tablets. Alternatively, manufacturing parameters can be correspondingly adjusted. If the quality parameters meet predefined requirements, the process flow may be maintained constant.

Alternatively, the apparatus may be operable at-line of the process of producing a pharmaceutical product. In such a configuration, a sample from the material produced during a pharmaceutical process can be taken and can be analyzed independently from and outside of this manufacturing process. This has the advantage that a sample with a very small thickness, and inserted into a very small sample holder may be analyzed which can be advantageous from the point of view of accuracy of the measurement results.

In an embodiment, the control unit may be adapted for assigning the granulate to one of a plurality of quality classes indicative of the granulate's suitability for the production of tablets. The assigning may be performed based on an application of one or more criteria to the derived information. The control unit may be adapted for controlling the process of producing the pharmaceutical product based on the result of the assigning. In other words, the quality of the granulate for pressing tablets can be classified using the compressibility and/or dissolution characteristic and/or morphology. Two or more classes may be predefined, for instance based on reference measurements on reference granulates. Exemplary classes are "suitable for pressing tablets", "insuitable for pressing tablets", "appropriate for pressing tablets only after refinishing operation". Also a classification in accordance with a quantitative quality range (for instance on a quality scale between 1 and 10) is possible. Exemplary criteria may be "is compressibility in a range between . . . and . . . ?", "is dissolubility in a range between . . . and . . . ?", "is a percentage of the physiologically active substance in an amorphous phase larger than . . . ?". The control unit may then control the tablet pressing procedure in accordance with the result of the classification.

The X-Ray measurement can be performed in reflection or in transmission. The measurement time may be in the order of magnitude of seconds, for instance 100 s.

In the following, further exemplary embodiments of the method will be explained. However, these embodiments also apply to the apparatus, to the computer-readable medium and to the program element.

In an embodiment, the method may comprise analyzing a granulate consisting of multiple solid components having physiologically (pharmaceutically) active substance and a gastric juice resistive spray. Therefore, it is particularly possible with the disclosed method and evaluation architecture to analyze coated granulates which have a core with a physiologically active substance and a shell of a material which is resistive to gastric juice. Such a protective shell is sometimes applied to a pharmaceutical substance to prevent that the physiologically active substance is already released in the gastric, and not at a desired destination such as the intestine.

The method may allow to analyze a dry granulate. Alternatively, a coated granulate may be analyzed as well, since it has been recognized that the sensitivity of the X-ray scattering method, i.e. a sensitivity with regard to electron density, is not negatively impacted when additional components are added to a sample.

According to a preferred embodiment, the results from the X-ray scattering analysis may be used, optionally in combination with a database of measurement data, to model a way a pressed tablet will be dissolved by gastric juice/in the intestine. Therefore, a model of the functioning of a tablet can be obtained from the measurement data.

The term "particle" may be understood as a predominantly near spherical structure of a macromolecular size, and coated particles may in the following be referred to as granules. A liquid coating composition may comprise a solvent, particularly water, and coating materials, for instance a polymer (particularly polyacrilate). Coating of a granulate is a usual preparation procedure of pharmaceuticals before being compressed into tablets. The last step of granulation includes a complete coating procedure.

In one embodiment, a pharmaceutical granulate may be analyzed by X-ray diffraction so that quality parameters (such as information indicative of at least one of a compressibility and a dissolution characteristic) of more components in solid state applying Porod positive deviation. This is a very precise way for deriving information about electron density contrast not only between background and solid, but also in a solid state between each component.

However, it has turned out that, for a very fast analysis of a granulate constituted by a plurality of different pharmaceutical components in solid state, it is also possible to determine quality parameters (such as information indicative of at least one of a compressibility and a dissolution characteristic) with classical Porod law (two phases (here air and solid)) of the entire granulate, i.e. It has turned out that correspondingly averaged data can surprisingly still be indicative of the overall quality of the granulate for tablet formation or the like. Hence, particularly for high-throughput industrial applications, the characterization of multi-component granulates by averaged quality parameters is a fast and simple way of deriving still sufficiently meaningful results also by application of classical Porod low, since it still allows to understand relative tendencies or to consider percental differences between different samples.

The aspects defined above and further aspects of the invention are apparent from the examples of embodiment to be described hereinafter and are explained with reference to these examples of embodiment.

DESCRIPTION OF THE DRAWING

The invention will be described in more detail hereinafter with reference to examples of embodiment but to which the invention is not limited.

FIG. 2 shows a SAXS curve obtained from a measurement for the examples of Carbamazepine (CBZ) in a linear and in a logarithmic illustration.

FIG. 3 shows a Porod's range of the spectrum of FIG. 2.

FIG. 4 shows a Guinier's range of the spectrum of FIG. 2.

FIG. 5 shows an Invariant of the spectrum of FIG. 2.

FIG. 9 shows a SAXS pattern of a placebo mixture pills with an exposure time of 700 s captured and evaluated according to an exemplary embodiment of the invention.

FIG. 10 is a table showing a number of quality control parameters with regard to compressibility of a pharmaceutical granulate derived from the spectrum according to FIG. 9.

FIG. 11 shows SAXS spectra of different samples of a placebo mixture granulate with an exposure time of 700 s captured and evaluated according to an exemplary embodiment of the invention.

FIG. 15 shows WAXS spectra of the different samples according to FIG. 13 and FIG. 14 evaluated according to an exemplary embodiment of the invention.

FIG. 16 shows SAXS spectra of different samples comprising Carbamazepine coated granulate with an exposure time of 100 s captured and evaluated according to an exemplary embodiment of the invention.

FIG. 19 shows a diagram illustrating the dependency between a dissolution time and a percentage of released material for different samples evaluated according to an exemplary embodiment of the invention.

FIG. 20 shows two diagrams illustrating two SAXS quality parameters for the different samples of FIG. 19 according to an exemplary embodiment of the invention.

DESCRIPTION OF THE PREFERRED EMBODIMENT

Figure 1:
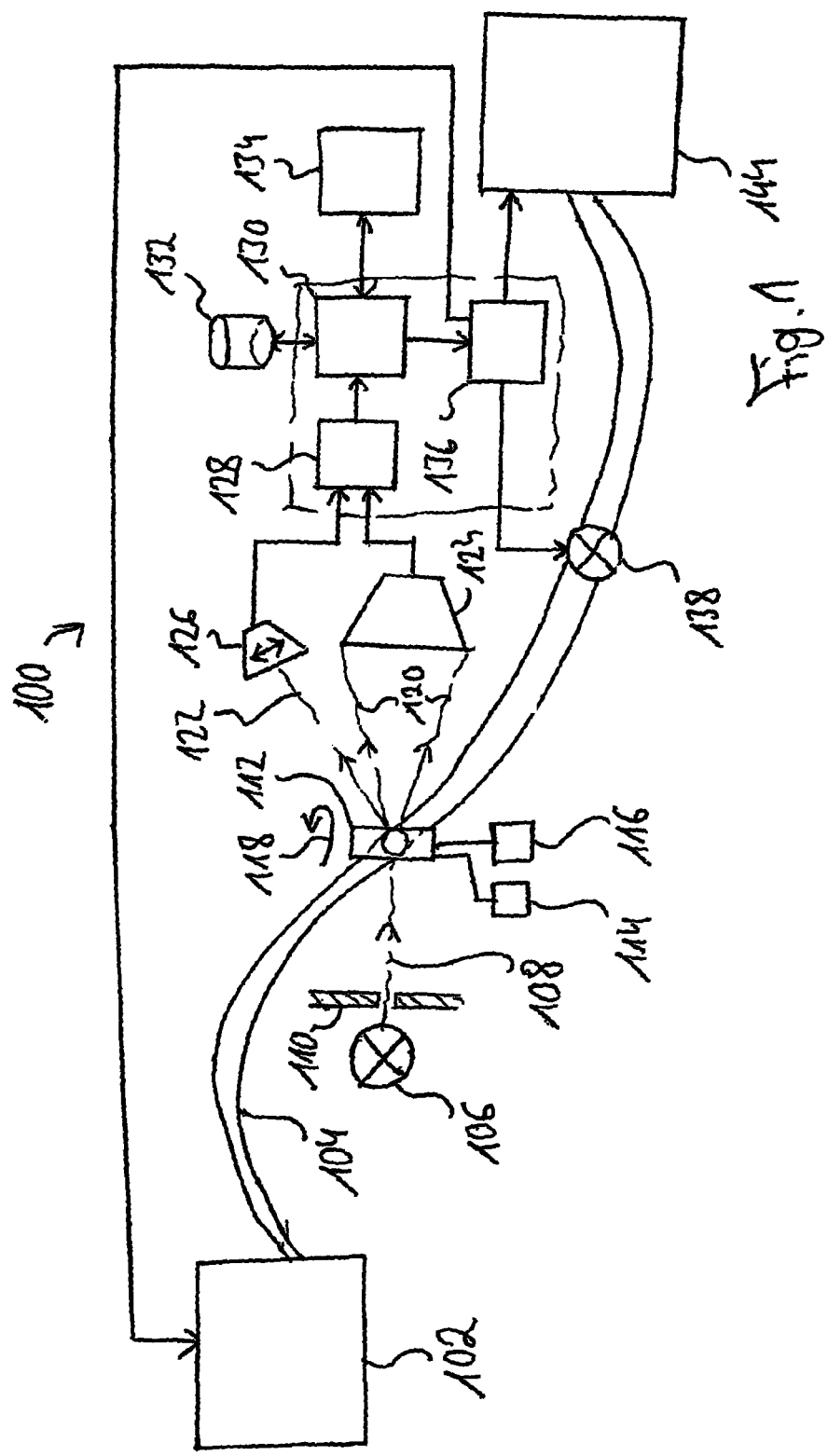
FIG. 1 illustrates a system for analyzing granulate material according to an exemplary embodiment of the invention.

The illustrations in the drawings are schematical. In different drawings, similar or identical elements are provided with the same reference signs.

It has been recognized that, in contrast to conventional analysis methods of investigating pharmaceutical granulates, a "total" inner surface can be determined by X-ray, i.e. a surface including a contribution of closed pores. SAXS provides analytical porosity in the "nano" range where the Van der Waals and adhesion interaction forces become important and effective. In addition, the X-ray method observes simultaneously the information of a polymorphic state of the meter. Hence, X-ray diffraction may be advantageously implemented in a pharmaceutical granulate process control, particularly in coated-granulate homogeneity process control.

Physical and physico-chemical parameters form an integrated part of the quality specification in the pharmaceutical granulate process, because they play an essential role in the technical and economic aspects of production. Small- and Wide-Angle X-Ray Scattering (SWAXS) may be used to test some essential properties of powders and granulates used in the production of compressed tablets.

Experimental observations show that the absolute intensities in the SAXS range differ with those good and badly compressible samples, whereby the transmission values are equal. The "good" compressible sample shows more intensity in the SAXS range verified by determination of the scattering power and calculation of the second moment integral (invariant).

Without wishing to be bound to a specific theory, it is presently believed that the "good" compressible samples pose a higher nano-porosity of granulates (under polarizations microscopy appears as more fine granulate distribution) and therewith more total inner surface, which leads to higher absolute intensities of the SAXS scattering curves and lower correlation length (L) of nano domains in material.

Particularly the following aspects can be seen as advantageous exemplary embodiments:

Process control: monitoring of the granulation process in exposure time of seconds, due to the comparison with measured references. Early detecting and evaluation of deviations of absolute scattered intensity in the SAXS range with "Invariant" (Q), Porod constant (K) and nano porosity as a granulate homogeneity, compressibility and dissolution control indication.

Simultaneously monitoring of API and granulate crystallinity or amorphism by WAXS. In some cases even determination of API polymorphic state (for instance Carbamazepine).

Fast measurements allow a control between all granulating steps and for all kind of granulates (i.e. dry or coated).

Possibility of a direct coupling with a DSC (Differential scanning calorimetry) or pressure-cell (available, for instance, from HECUS GmbH) for indication of additional analytical parameters.

Possibilities for at-line granulating process implementation of the method, wherein an inline measuring procedure is also possible, according to short measuring time and the low radiation energy (typically 8 KeV but any other suitable X-ray energy can be used), which causes no material damage.

Decrease of the expenditure for laboratory analytics.

Hence, a gist of an exemplary embodiment of the invention is the implementation of a SWAXS method for continuous or periodic quality control of pharmaceutical granulates. Screening of measured absolute scattered intensity in a time range of seconds may be performed, as an indication for granulates nano porosity, homogeneity distribution of the coating lack, dissolution and compressibility. Good compressible granulate shows a higher SAXS scattered intensity due to higher electron density fluctuations of finer nano-porosity. A simultaneous monitoring of crystallinity or amorphism by WAXS can be performed as well.

As compared to conventional approaches, this may result in the following advantages:

Improvement of process quality by fast measured parameters.

improved analytics makes regulation possible before large amount of the material has to be rejected.

Improves product yield by optimization of the process quality.

Reduced expenditure for time and cost-intensive off laboratory analytics.

In an embodiment, the Invariant (Q), Porod constant K and/or Porod law deviation determination in pharmaceutical granulates may be used as a process quality control factor. Due to formula application of Porod law positive deviation, this allows to analyze all kinds of granulates. Such an approach is much more specific for the determination of the granulate compressibility as compared to conventional mechanical systems.

A system according to an exemplary embodiment of the invention may be used as a standard pharmaceutical process analysis and basic research for also theoretical explanations.

A software tool may be provided for immediate monitoring of the Invariant (Q), Porod positive law deviation constant (K), direct proportionality to total inner surface (K/Q) and correlation length (L) parameter as quality control.

Experimental results of the connections between desired and undesired process changes of the granulation may be stored in a database which may be accessed by the process control system for a comparison of actual data of an analyzed sample and reference data taken from the database.

In the following, referring to FIG. 1, an apparatus 100 for analyzing a granulate for producing a pharmaceutical product according to an exemplary embodiment of the invention will be explained.

The apparatus 100 comprises a schematically illustrated granulate container 102 in which a pharmaceutical granulate is manufactured or stored. Manufacture may include the coating of a physiologically active substance with a polymer preventing release of the pharmaceutically active agent in gastric juice. The granulates may have a size of, for instance, 10 μm, and may be conveyed via a conveying unit 104 (such as a hose, a conveyor belt or the like, in which the granulates are transported) to an X-ray scattering apparatus. The X-ray scattering apparatus comprises an X-ray source 106 adapted for generating a primary X-ray beam 108 having X-rays with an energy of, for instance, 8 keV (but any other suitable X-Ray energy can be used). The primary X-ray beam 108 is passed through an aperture 110 and then reaches a sample container 112 which may be filled with the conveyed granulate. For instance, the granulate can be guided through the conveying channel 104 continuously, so that a continuous monitoring of the quality of the granulate can be performed with the X-ray apparatus. Alternatively, a test volume of the granulate may be diverted from the conveyed material, may be inserted into the sample container 112 and may be subjected to a granulate quality measurement before the conveying process continues.

The sample container 112 is coupled with a temperature control unit 114 adapted for controlling the temperature of the sample during the analysis. Applying a temperature profile to the sample during the measurement allows to obtain additional information. By a pressure control unit 116, a predefined pressure profile can be applied to the granulate during the X-ray analysis.

The primary X-ray beam 108 is scattered on the granulate material in the sample container 112. The sample container 112 can be rotated during the measurement, as indicating by an arrow 118. It has turned out that rotation of the sample in the sample container 112 during the measurement increases the accuracy.

The primary X-ray beam 108 is scattered at the granulate in the sample container 112 under small angles (see reference numeral 120) and under large angles, see reference numeral 122. The secondary X-ray beams 120 scattered under small angles will be detected by a first detector 124 which can be a spatially fixed array of pixel elements. The wide angle scattered X-rays 122 can be detected by a second detector 126. In the shown embodiment, the wide angle detector 126 can be spatially moved to sample the wide angular range. Hence, the measurement at both small angles and large angles may be performed at the same time.

The measurement results obtained by the detectors 124, 126 are forwarded to a data receiving unit 128. The data receiving unit 128 is adapted for receiving the X-ray diffraction data from the detectors 124, 126 indicative of a scattering of the X-rays 108 irradiated onto the granulate in the sample container 112. The data receiving unit 128 may pre-process these data and may forward them to a processing unit 130.

The processing unit 130 is coupled with the data receiving unit 128 and is adapted for processing the X-ray diffraction data to derive information with regard to compressibility, dissolution rate, morphology and/or homogeneity of the granulate. In this context, it is also possible that the processing unit 130 bidirectionally communicates with a database 132, such as a mass storage device. The database 132 may include a data set correlating X-ray data with compressibility, dissolution rate, morphology and/or homogeneity properties of reference samples. The processing unit 130 may query the database 132 for the best fit of the present X-ray diffraction data with corresponding data of a reference sample. The processing unit 130 may then conclude that properties of the presently measured sample corresponds to the properties of the best fitting reference sample.

An input/output unit 134 is also be bidirectionally coupled to the processor unit 130 so as to enable a user or operator to provide the processor unit 130 with instructions and to receive the result of the analysis.

The result of the processing performed by processor 130 may be forwarded to a control unit 136 for controlling the process of producing pharmaceutical products (such as tablets) from the granulate based on the derived information. The control unit 136 will use the granulate quality data received from the processing unit 130 and will, based on this, provide control signals to the granulate container 102 in case that a granulate formation process has to be modified to improve the quality. It is also possible that the control unit 136 controls a valve 138 (arranged in the conveyor unit 104) to be closed so as to stop a manufacturing process, for instance if the quality of the granulate with regard to tablet production is below an acceptable level. Also, the granulate conveyed through the conveying unit 104 can be conveyed downstream of the X-ray scattering apparatus to supply the granulate, after approval by the shown analysis system, to a tablet processing block 144 which then can produce tablets from the granulate. The physical stability of tablets depends, inter alia, on coating homogeneity. At present, no suitable tool can follow and qualify homogeneity distribution of a coating spray on granulating material. According to the described embodiment of the invention, Small- and Wide-Angle X-Ray Scattering (SWAXS) may be applied to display the process.

Although many of the components of the apparatus 100 are shown as separate blocks in FIG. 1, it is also possible to integrate several of them into one unit. For instance, it is possible to integrate at least a part of the units 128, 130, 136 into a single processor.

Peaks in the wide angle scattering spectrum as detected by detector 126 may allow to determine morphology, particularly a crystalline or amorphous state, of the physiologically active substance of the granulate. Simultaneously, the small angle scattering data received by detector 124 can be evaluated so as to determine information with regard to compressibility and dissolution rate of the granulate in a physiological object such as a human being.

For SWAXS (SAXS and WAXS) measurements, a high-flux laboratory Small and -Wide Angle X-ray scattering camera S3-Micro (Hecus X-Ray Systems, Graz Austria) may be used which is equipped with a high-brilliance micro-beam delivery system operating at a low power of 50 W (50 kV and 1 mA), with point-focus optics (FOX3D) and with 1D- or 2D-detection system combined with automatized data evaluation software. A usable X-ray wavelength is 1.54 Å and the SAXS-curves (scattered intensities as a function of the scattering angle 2θ) can be recorded with a 1D-detector (PSD-50, Hecus X-ray Systems, Graz, Austria) in the angular range $0.06°<2θ<8°$. The calibration of the q-scale (calibration of the detector pixels to the respective scattering angle) may be done by measuring silver-behenate with a defined lamellar spacing of 58.38 Å, where q—the reciprocal scattering vector—is related to the scattering angle 2θ by $q=4\pi*\sin θ/λ$. Furthermore, the invariant (Q) may be used as an indicator parameter for homogeneity of the coating material on granulates. It is the integral of the second moment of the SAXS scattering curve from angle 0 to infinity, whereas the scattering of angle 0 and toward infinity is done by special extrapolation (a Guinier extrapolation towards 0 angle and a Porod extrapolation towards infinity angle). The Q is named the invariant because it does not depend on the structure but only on the volume fraction and contrast. For measurements, the samples can be filled into glass capillaries of 2 mm inner diameter. Measurements may be performed at room temperature with an exposure time of 100 sec.

An exemplary system of studies are Carbamazepine (CBZ) granulates, which can be obtained from the firm GL-Pharma (Lannach, Austria) after occurring of tablet-pressing problems in a process production i.e. granulate-samples with not well tablet compressible properties. Two main components of the system are crystalline CBZ and amorphous L30D as a polyacrylat coating spray. Measurements with a good and bad compressible CBZ coated granulate have been performed. Already after 100 seconds of exposure time, it turned out to be possible to obtain different scattered intensity in the SAXS range, whereas the transmission values are the same. After determination of the integral scattering power and calculation of the second moment integral (invariant), it is possible to display an invariant difference between the well and unwell compressible samples by a multiplicative factor of 4. Apparently an inhomogeneous distribution of gastric juice resistant coating spray over granulates leads to lower SAXS scattered intensity and therewith to lower invariant value.

Next, it will be described in detail as to how the measurement data may be evaluated to derive meaningful information.

In the following, spectra obtained by SAXS will be explained in combination with a corresponding evaluation method.

FIG. 2 shows a diagram 200 having an abscissa 202 along which the absolute value of the scattering vector (q-value) is plotted. Along an ordinate 204, the intensity is plotted in arbitrary units. Furthermore, FIG. 2 shows a diagram 250 which is similar to diagram 200 but illustrates, along ordinate 252, the logarithm of the intensity.

FIG. 2 hence shows SAXS curves obtained from a measurement for the examples of Carbamazepine (CBZ) in a linear and in a logarithmic illustration.

FIG. 3 shows a diagram 300 having an abscissa 302 along which the logarithm of the q-value is plotted. Along an ordinate 304, the logarithm of the intensity is plotted. FIG. 3 illustrates the Porod's range of the measured spectrum. The calculated value of K (Porod constant) is proportional to the decay of the scattered SAXS intensity towards larger angles.

FIG. 4 shows a diagram 400 having an abscissa 402 along which the square of the q-value is plotted. Along an ordinate 402, the logarithm of the intensity is plotted. FIG. 4 illustrates Guinier's range of the spectrum.

FIG. 5 shows a diagram 500 having an abscissa 502 along which the q-value is plotted. Along an ordinate 504, the product of intensity and the square of the q-value is plotted. FIG. 5 shows the invariant of the spectrum. The integral scattering, the so-called invariant, is equal to the total irradiated volume times the mean-square electron density fluctuation—independently of a domain shape.

Next, an evaluation of the spectra shown in FIG. 2 to FIG. 5 and Porod's Law Deviation will be explained.

Powder SAXS characterization may be determined by the assumption that the geometry is Euclidian (non-fractal), with a simple correlation between the angular dependence of the inner surface and the scattering intensity:

$$\lim_{q\to\infty} I(q) = k/q^4$$

In this equation, q is the modulus of the scattering vector ($q=4\pi*\sin θ/λ$). A scattering angle is 2θ, and λ is the wavelength of the X-rays. I(q) is the scattering intensity at q, k can be denoted as the tail end constant.

Another property derived from the scattering experiment is an indicator for the scattered intensity and is defined as the integral of zero-th moment of the SAXS scattered curve from angle 0 to infinity $$M0 = \int_0^\infty I(q) dq$$

A further property derived from the scattering experiment is the so-called invariant Q:

$$Q = \int_0^\infty I(q) q^2 dq$$

The mathematical relation or quotient between k and Q (k/Q) gives a factor directly proportional to the specific total inner surface (Si) of the material with φ as volume fraction $$Si = \pi \frac{k}{Q} \varphi(1-\varphi)$$

The average distance any straight line takes through the system without encountering the interface is:

$$\bar{l} = \frac{4Q}{\pi k}$$

It is noted that "l" according to the previous equation will also be denoted as "L" in the following.

Figure 6:
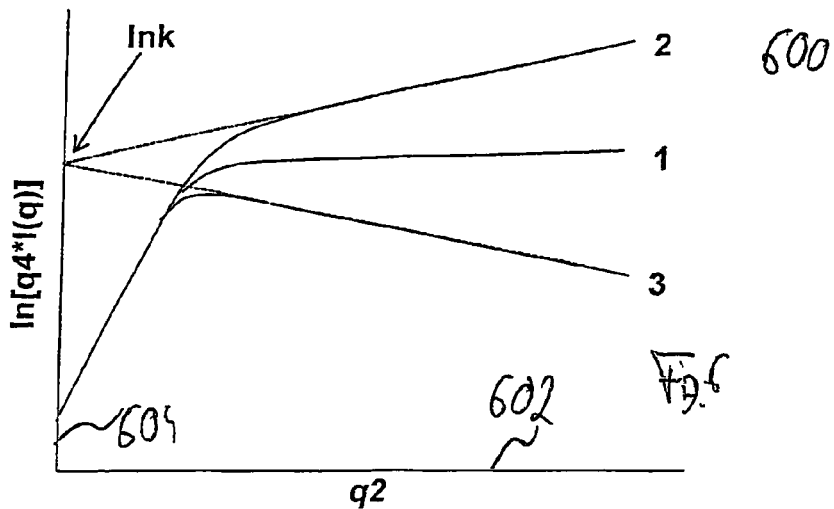
FIG. 6 shows different Porod plots with and without a deviation from the Porod Law.

FIG. 6 shows a diagram 600 having an abscissa 602 along which the square of the q-value is plotted. Along an ordinate 604, the logarithm of the forth power of the q-value multiplied with the intensity is plotted. Plot 1 shows a Porod plot with no deviation from Porod's law, plot 2 shows a Porod plot with a negative deviation, and plot 3 shows a Porod plot with a positive deviation of the Porod's law.

$$\ln[q^4 I(q)] = \ln k + q^2 \xi^2$$

In the latter equation, k is the Porod constant and $\xi$ is a parameter in relation to the size of the electron density inhomogeneity of the solid phase.

Figure 7:
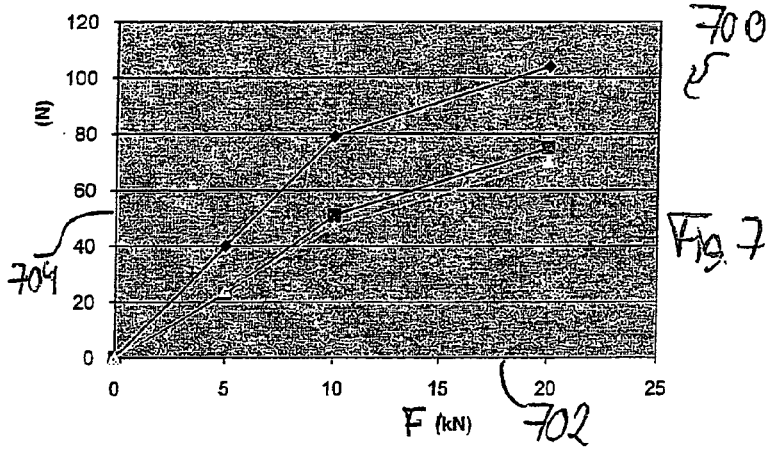
FIG. 7 shows a correlation between a tablet pressing force and a hardness of the resulting tablet for different samples.

FIG. 7 shows a diagram 700 having an abscissa 702 along which a pressure force for pressuring a tablet from a placebo mixture granulate is shown. Along an ordinate 704, the hardness of a pressed tablet is plotted. A corresponding correlation is shown for three different mixtures for material of the tablet. The used placebo material according to FIG. 7 includes 49% mass fraction lactose monohydrate, 49% mass fraction microcrystalline cellulose, 1% mass fraction silicon dioxide and 1% mass fraction magnesium stearate.

Figure 8:
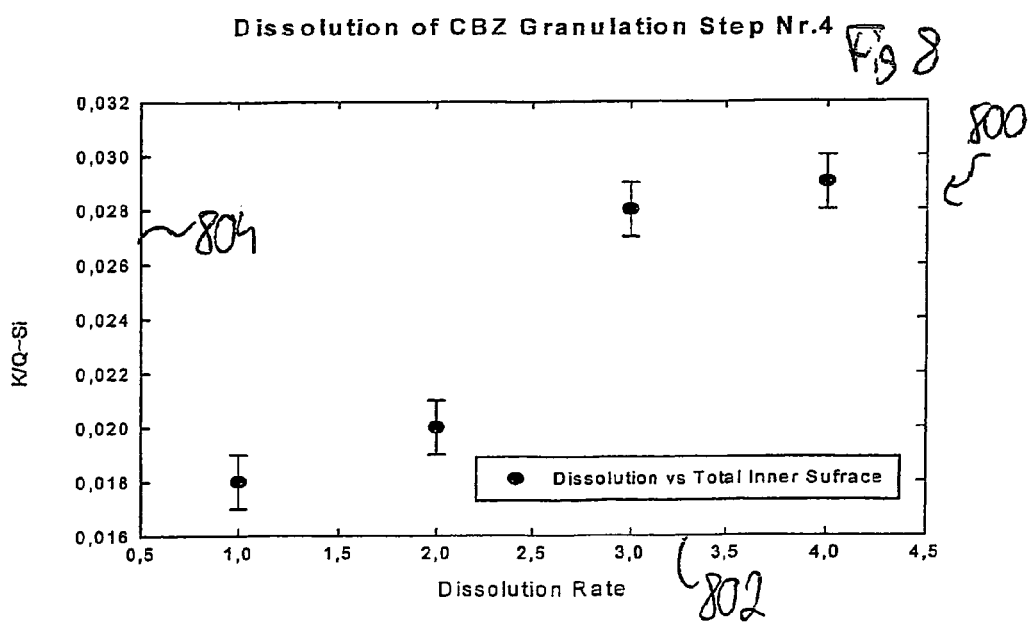
FIG. 8 illustrates a monitoring of a dissolution relevant step by Carbamazepine granulation by SWAXS methodology.

FIG. 8 shows a diagram 800 having an abscissa 802 along which a dissolution rate is plotted. Along an ordinate 804, a measure for a total inner surface is plotted. FIG. 8 shows that there is a clear correlation between dissolution rate and total inner surface. Thus, the total inner surface measurable with X-ray scattering may allow to derive information indicative of a dissolution characteristics of a medication. FIG. 8 shows the monitoring of a dissolution relevant step by Carbamazepine (CBZ) granulation by SWAXS methodology. The property may be a function of granulate total inner surface due to granulate preparation.

As an example for granulation of CBZ, the following granulation steps may be performed:

Step 1: providing pure Carbamazepine
Step 2: moistening of 180 kg Carbamazepine with 12 kg Eudragit RSPO and diluted EtOH in a mixing device
Step 3: 40 minutes drying Carbamazepine with 12 kg Eudragit RSPO
Step 4: sieving Carbamazepine, Eudragit RSPO with 2 mm Conidur
Step 5: adding 6 kg Talc and 0.6 kg Magnesium Stearate to Carbamazepine, Eudragit RSPO; 60 minutes particle coating with L30D
Step 6: 120 minutes spraying with L30D
Step 7: 180 minutes spraying with L30D
Step 8: spraying 150 kg with L30D
Step 9: post-drying
Step 10: 2.4 mm sieving, plus 23.4 kg MCC, 24 kg Sodium Carboxy Methyl Starch, 2.4 kg Aerosil 200, 0.6 kg Magnesium Stearate According to an exemplary embodiment of the invention, the X-ray analysis may be performed directly after step 10, since the granulate is then completely finished and ready for tablet pressing. Additionally or alternatively, it is also possible to perform such a measurement at any one of the other steps. For example, proper quality of an active ingredient may also be measured in step 1.

With regard to SAXS, the theory of Porod's law positive deviation is well applicable for SAXS quality control of granulates i.e. coated or dry. Quality parameters such as Porod-exponent, invariant, total inner surface and correlation length provide relevant information about granulation compressibility, dissolution and coating homogeneity distribution. Additional monitoring of polymorphisms may be performed simultaneously by WAXS. Temperature scans may be run for purity and polymorphism tests.

In the following, placebo studies will be illustrated to prove the theoretical behavior and even to extend experiments for generate granulates, coated or dry.

FIG. 9 shows a diagram 900 having an abscissa 902 along which the q-value is plotted. Along an ordinate 904, the intensity is plotted in arbitrary units. The three shown X-ray scattering curves relate to three different pressing forces applied during forming pills from the placebo material.

Hence, FIG. 9 shows SAXS spectra of such placebo mixture pills with an exposure time of 700 s. In the SAXS spectra, 5 kN, 10 kN and 20 kN represent the pressure strength for the same amount of the placebo material, respectively.

FIG. 10 shows a table 1000 in which a correlation between the different parameters which can be derived from X-ray scattering on the one hand and the pressing force on the other hand can be seen. Hence, there is a clear correlation between the experimental values and the pressing force. FIG. 10 therefore shows a table 1000 of quality control parameters: K2 denotes the Porod constant, Q denotes the invariant, K/Q is a figure which is directly proportional to a total inner surface, and L corresponds to an average correlation length. The calculated Porod constant K, invariant Q, parameter direct proportional to total inner surface K/Q and correlation length L allow to distinguish between good and bad compressible samples. Invariant Q is corresponding by a multiplicative factor of 4±0.5.

FIG. 11 shows a diagram 1100 which has similar properties as diagram 900 of FIG. 9. FIG. 11 shows SAXS spectra of a placebo mixture granulate with an exposure time of 700 s. The SAXS pattern of placebo mixture granulate relates to S1-pure placebo powder mixture, S2-granulate after milling the pills obtained from S1, and S3-granulate after milling the pills obtained from S2.

Figures 12, 13, 14:
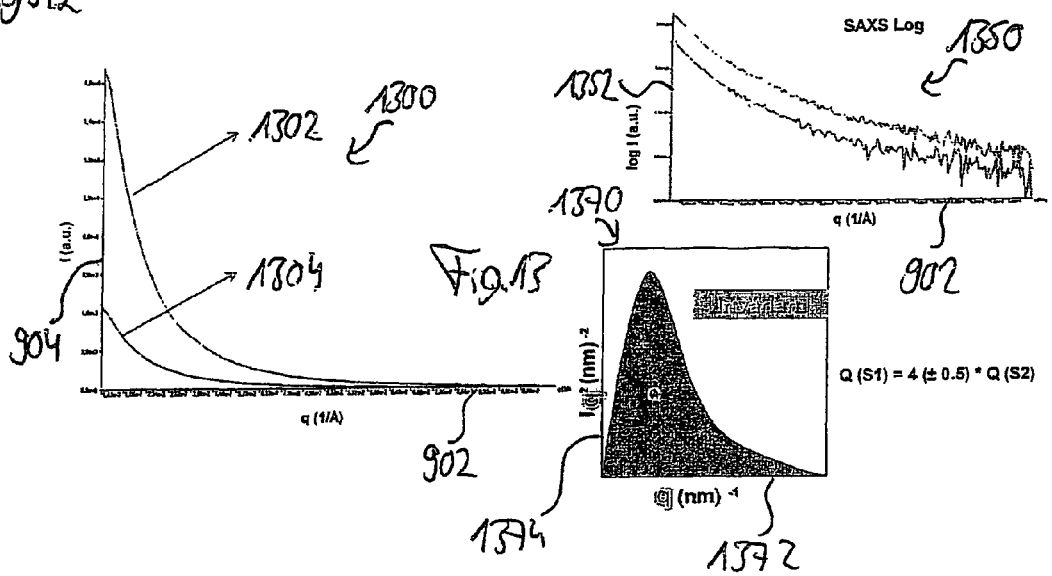
FIG. 12 is a table showing a number of quality parameters with regard to compressibility of the samples according to FIG. 11.
FIG. 13 shows SAXS spectra of different samples of a Carbamazepine coated granulate with an exposure time of 700 s captured and evaluated according to an exemplary embodiment of the invention.
FIG. 14 is a table showing a number of quality parameters with regard to the different samples derived from the spectra according to FIG. 13.

Table 1200 shown in FIG. 12 shows similar parameters as table 1000 shown in FIG. 10. FIG. 12 shows quality control parameters in accordance with FIG. 11.

FIG. 13 shows SAXS spectra of a CBZ coated granulate with an exposure time of 700 s, and FIG. 14 shows a table with quality-related parameters derived from the SAXS spectra of FIG. 13.

FIG. 13 illustrates how a good sample (S1) and a bad sample (S2) in terms of the fabrication of tablets from granulates can be distinguished in a SAXS measurement. More precisely, (S1) and (S2) represent a good and a bad compressible CBZ coated granulate, respectively. Again, a spectrum 1300 in FIG. 13 is similar to spectra 900 and 1100. Reference numeral 1302 relates to a good sample, whereas reference numeral 1304 relates to a bad sample. With an exposure time of 300 seconds, the logarithmic spectra shown in diagram 1350 can be obtained by SAXS. An ordinate 1352 shows the logarithm of the intensity. A diagram 1370 shows the q-value on an abscissa 1372 and shows the product of the intensity and the square of the q-value along an ordinate 1374. The invariant Q, which serves a quality parameter, corresponds to the area of under the curve as shown in the diagram 1370.

Table 1400 shown in FIG. 14 corresponds to the measurements of FIG. 13 and shows similar parameters as tables 1000 and 1200.

FIG. 15 shows a WAXS spectrum in a diagram 1500 having an abscissa 1502 showing the scattering angle, whereas an intensity is plotted along an ordinate 1504. Spectrum 1500 shows distinct peaks 1506 and in addition an underground 1508. A comparison between the two curves 1510, 1512 shown in FIG. 15 indicates that the sample relating to curve 1510 has a larger amount in the amorphous state than the sample relating to curve 1512 which has a smaller amount in the amorphous state. This allows identifying curve 1510 as relating to a good sample and curve 1512 as relating to a bad sample in terms of tablet fabrication.

Since curve 1510 corresponds to sample (S1) and curve 1512 corresponds to sample (S2), it can be concluded that the WAXS pattern of FIG. 15 confirms the results of the SAXS pattern of FIG. 13. One can identify the polymorphic state III.

Furthermore, the calculated invariant difference between the good and bad compressible sample corresponds to a factor of 20±1.0

The simultaneously obtained WAXS spectra of FIG. 15 show clearly more amorphous content in the good compressible sample (S1) displaying a higher intensity in the horizontal spectral line 1508 but lower intensity in the sharp Bragg peaks 1506 originated from the crystalline lattes of the compound. Without wishing to be bound to a specific theory, it is presently believed that a better homogeneous distribution of the L30D amorphous polyacrylat spray on the CBZ granulates leads to a higher amorphous content in the system, which may be also accompanied by more amorphous signal visible on WAXS pattern.

Figure 17:
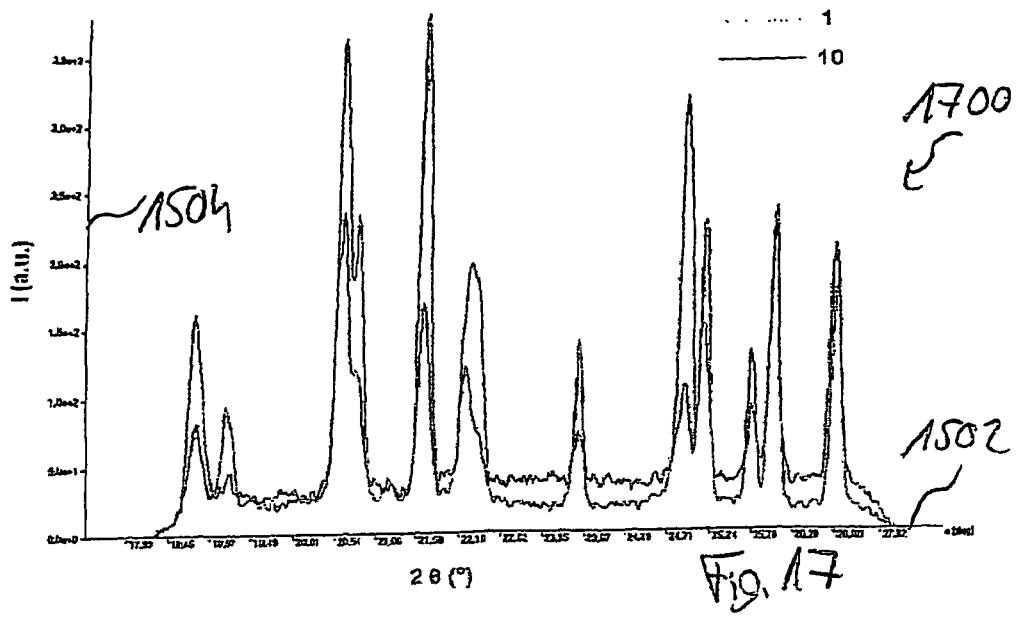
FIG. 17 shows WAXS spectra of the different samples according to FIG. 16 evaluated according to an exemplary embodiment of the invention.

FIG. 16 and FIG. 17 illustrate a SWAXS pattern of a CBZ coated granulate with an exposure time of 100 s. More precisely, FIG. 16 shows a SAXS pattern, wherein (1) represents pure CBZ (Aceto) and (10) represents a good compressible CBZ coated granulate, respectively. FIG. 17 shows a corresponding WAXS pattern for species (1) and (10), respectively.

More particularly, FIG. 16 shows curves 1600, 1650, 1670 which are similar to curves 1300, 1350, 1370, respectively, but relate to a different material. FIG. 17 shows a diagram 1700 which is similar to the diagram 1500, but concerns a different sample.

Thus, referring to the above-described sequence of ten steps for manufacturing granulates, scattered intensity in SAXS regime of the pure CBZ (1) is compared to the last step (10) of granulation. An invariant determination shows a difference between the pure CBZ and last CBZ granulation step by a multiplicative factor of 20. In the WAXS regime, again more content of amorphous state in the last granulation step is obtained due to addition of the amorphous L30D polyacrylat spray. This is clearly visible by more signal intensity in the bottom and less signal intensity in the peak positions.

Figure 18:
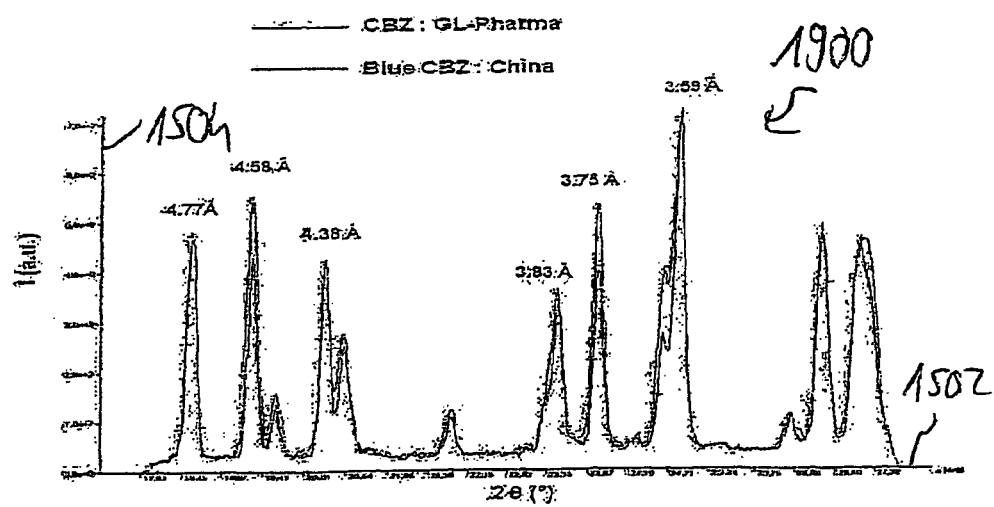
FIG. 18 shows WAXS spectra of different samples evaluated according to an exemplary embodiment of the invention.

FIG. 18 shows a diagram 1900 which is similar to FIG. 17 and allows to distinguish different quality levels of two CBZ samples (pure CBZ powder and good compressible CBZ coated granulate). FIG. 18 shows WAXS spectra of the different samples evaluated according to an exemplary embodiment of the invention.

In general, an analytical method is disclosed which allows to perform quality control in term of nanoporosity, tableting and compressibility, dissolution behavior and polymorphism for all kind of pharmaceutical granulates (coated or dry). Thus, the quality control parameters (K, Q, K/Q, L) may be followed in the seconds-range measuring time of any granulating step by a manufacturing procedure. Simultaneously, it is possible to display a crystalline or an amorphous state of granulate and follow a polymorphic state due to Bragg peaks. Furthermore, the method is independent of granulate solid-state complexity (if it is dry or coated, if it is lower or higher number of components in solid-state) due to the proposed formula for positive deviation of the Porod law.

The inventive concept applied to the above example of CBZ may be applied to any other pharmaceutical granulate material as well. Due to the investigation data of the "real life" CBZ example, one may conclude the following process control rules for this kind of CBZ manufacturing procedure:

If an analyzed sample displays an invariant value 4±0.5 times (FIG. 9) smaller than the reference ("good" sample) the granulation process has to be stopped. Otherwise a huge amount of expensive material (sometimes several hundred kilos) has to be rejected.

If an analyzed sample displays an invariant value 20±1.5 times (FIG. 10) higher than the pure API (Carbamazepine) the granulation process may be successful. Afterwards, a last granulation step will show a good compressibility into tablets.

FIG. 19 shows a diagram 2000 illustrating a dependency between a dissolution time plotted along an abscissa 2002 and a percentage of released material plotted along an ordinate 2004 for a VCH003/10 Pentoxi 09/2584 sample (sample 1) and for a VCH029/10 Pentoxi 10/0281 sample (sample 2) both comprising pentoxifylline and being evaluated according to an exemplary embodiment of the invention.

FIG. 20 shows a first diagram 2100 and a second diagram 2150 illustrating k/Q (reference numeral 2160) and correlation length L (reference numeral 2170) as SAXS quality parameters for sample 1 and sample 2 of FIG. 20.

FIG. 19 and FIG. 20 show that the SAXS analysis allows for a dissolution prediction. The granulate of sample 1 shows higher dissolution in released % than the granulate of sample 2. At the same time, the granulate of sample 1 shows higher k/Q values (indicative of the total inner surface) and therewith higher nanoscopical total inner surface than the granulate of sample 2.

Hence, FIG. 19 and FIG. 20 provide experimental evidence that there exists a close correlation between SAXS quality parameters on the one hand and the dissolution characteristics on the other hand.

Concluding, SAXS quality parameter such as first momentum (MO), invariant (Q), total nanoscopic inner surface (K/Q) and correlation length (L) provide information about granulate dissolution behavior. A higher total inner surface (higher K/Q and lower L) of granulate may lead to better tablet dissolution.

Simultaneous, it is possible by WAXS to observe no changes of the API "finger prints" after producing the granulates.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

Implementation of the invention is not limited to the preferred embodiments shown in the figures and described above. Instead, a multiplicity of variants are possible which use the solutions shown and the principle according to the invention even in the case of fundamentally different embodiments.

We claim:

1. An apparatus for analyzing a granulate for producing a pharmaceutical product, the apparatus comprising:
    a data receiving unit structured for receiving X-ray diffraction data indicative of a scattering of X-rays irradiated onto the granulate, the X-ray diffraction data resulting from Small Angle X-Ray Scattering;
    a processor unit structured for processing the X-ray diffraction data to derive information indicative of at least one of a compressibility and a dissolution characteristic of the granulate, the processor unit thereby being structured to derive at least one of a second momentum integral of a measurement spectrum and a Porod constant; and
    a control unit structured for controlling a process of producing a pharmaceutical product based on the derived information.

2. The apparatus of claim 1, wherein the processor unit is structured for processing the X-ray diffraction data to derive information regarding different components of a granulate consisting essentially of multiple solid components.

3. The apparatus of claim 1, wherein the data receiving unit is also structured for receiving X-ray diffraction data resulting from Wide Angle X-Ray Scattering.

4. The apparatus of claim 3, wherein the processor unit is structured for processing the Wide Angle X-Ray Scattering data to derive information indicative of a quality-related property of a physiologically active substance of the granulate, a property indicative of a morphology, a crystalline state or an amorphous state of the physiologically active substance.

5. The apparatus of claim 4, wherein the processor unit is structured for processing the X-ray diffraction data to derive information indicative of a quality of the granulate for producing a pharmaceutical product based on an intensity of a measurement spectrum constituted by the X-ray diffraction data.

6. The apparatus of claim 5, further comprising an X-ray source structured for irradiating the granulate with X-Rays of a suitable X-ray energy or with X-Rays having an energy of substantially 8 keV.

7. The apparatus of claim 1, further comprising a granulate container for accommodating the granulate and structured for rotation during acquisition of the X-ray diffraction data.

8. The apparatus of claim 1, further comprising a granulate container for accommodating the granulate and structured for subjecting the granulate to a predefined pressure profile during acquisition of the X-ray diffraction data.

9. The apparatus of claim 1, further comprising a granulate container for accommodating the granulate and structured for subjecting the granulate to a predefined temperature profile during acquisition of the X-ray diffraction data.

10. An apparatus for analyzing a granulate in order to produce a pharmaceutical product, the apparatus comprising:
   a data receiving unit structured for receiving X-ray diffraction data indicative of a scattering of X-rays irradiated onto the granulate, the X-ray diffraction data resulting from Small Angle X-Ray Scattering;
   a processor unit structured for processing the X-ray diffraction data to derive information indicative of at least one of a compressibility and a dissolution characteristic of the granulate, the processor unit thereby being structured to derive at least one of a second momentum integral of a measurement spectrum and a Porod constant; and
   a control unit structured for controlling a process of producing a pharmaceutical product based on the derived information, wherein at least one of the data receiving unit, the processor unit and the control unit are structured to be operated in-line with the process of producing the pharmaceutical product or at-line of the process of producing the pharmaceutical product.

11. The apparatus of claim 10, wherein the control unit is structured for assigning the granulate to one of a plurality of quality classes indicative of the granulate's appropriateness for production of tablets, wherein the assigning is performed based on an application of one or more criteria to the derived information, wherein the control unit is structured for controlling the process of producing the pharmaceutical product based on the result of the assigning.

12. A method of analyzing a granulate for producing a pharmaceutical product, the method comprising the steps of:
   a) receiving small angle X-ray diffraction data indicative of a small angle scattering of X-rays irradiated onto the granulate;
   b) processing the X-ray diffraction data to derive information indicative of at least one of a compressibility and a dissolution characteristic of the granulate;
   c) deriving at least one of a second momentum integral of a measurement spectrum and a Porod constant; and
   d) controlling a process of producing a pharmaceutical product based on the results of step c).

13. The method of claim 12, wherein the method comprises receiving X-ray diffraction data resulting from Wide Angle X-Ray Scattering.

14. The method of claim 13, wherein the method comprises processing the Wide Angle X-Ray Scattering data to derive information indicative of a quality-related property of a physiologically active substance of the granulate, a property indicative of a morphology, a crystalline state or an amorphous state of the physiologically active substance.

15. The method of claim 14, wherein the method comprises processing the X-ray diffraction data to derive information indicative of a quality of the granulate for producing a pharmaceutical product based on an intensity of a measurement spectrum constituted by the X-ray diffraction data.

16. The method of claim 15, wherein the method comprises using an X-ray source adapted for irradiating the granulate with X-Rays of a suitable X-ray energy or with X-Rays having an energy of substantially 8 keV.

17. The method of claim 12, wherein the method comprises analyzing a granulate consisting of multiple solid components or a granulate comprising at least a physiologically active substance and a gastric juice resistive spray.

18. The method of claim 17, wherein the method comprises analyzing a dry granulate or a coated granulate.

19. A computer-readable medium, in which a computer program of analyzing a granulate for producing a pharmaceutical product is stored, which computer program, when being executed by a processor, is structured to carry out or control the method of claim 12.

* * * * *